US008445201B2

(12) United States Patent
Laurent et al.

(10) Patent No.: US 8,445,201 B2
(45) Date of Patent: May 21, 2013

(54) HYBRIDIZATION DEVICE, METHODS, AND SYSTEM USING MIXING BEADS

(75) Inventors: Bellon Laurent, San Mateo, CA (US); Martin J. Goldberg, Saratoga, CA (US); Robert J. Lipshutz, Palo Alto, CA (US); Kaliyur Narasimhan, Saratoga, CA (US)

(73) Assignee: Affymetrix, Inc., Santa Clara, CA (US)

( * ) Notice: Subject to any disclaimer, the term of this patent is extended or adjusted under 35 U.S.C. 154(b) by 173 days.

(21) Appl. No.: 12/847,570

(22) Filed: Jul. 30, 2010

(65) Prior Publication Data

US 2011/0028352 A1 Feb. 3, 2011

Related U.S. Application Data

(60) Provisional application No. 61/230,268, filed on Jul. 31, 2009.

(51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl.
USPC ....... 435/6.1; 435/6.11; 435/91.1; 435/287.1; 435/287.2; 536/23.1; 536/24.3; 536/24.33

(58) Field of Classification Search
USPC .......... 435/6.1, 6.11, 91.1, 183, 283.1, 287.1, 435/287.2; 436/94, 501; 536/23.1, 24.3, 24.33; 422/50, 68.1
See application file for complete search history.

(56) References Cited

U.S. PATENT DOCUMENTS

| | | |
|---|---|---|
| 5,512,439 A | 4/1996 | Hornes et al. |
| 5,922,591 A | 7/1999 | Anderson et al. |
| 6,043,080 A | 3/2000 | Lipshutz et al. |
| 6,050,719 A | 4/2000 | Winkler et al. |
| 6,114,122 A | 9/2000 | Besemer et al. |
| 6,140,044 A | 10/2000 | Besemer et al. |
| 6,168,948 B1 | 1/2001 | Anderson et al. |
| 6,355,432 B1 | 3/2002 | Fodor et al. |
| 6,361,947 B1 | 3/2002 | Dong et al. |
| 6,386,749 B1 | 5/2002 | Watts et al. |
| 6,440,667 B1 | 8/2002 | Fodor et al. |
| 6,864,048 B2 | 3/2005 | Fodor et al. |
| 2002/0172965 A1* | 11/2002 | Kamb et al. ............ 435/6 |
| 2004/0086871 A1* | 5/2004 | Schembri ............ 435/6 |
| 2004/0120861 A1 | 6/2004 | Petroff |
| 2004/0235147 A1 | 11/2004 | Chappell |
| 2005/0142664 A1 | 6/2005 | Loney |
| 2005/0208120 A1* | 9/2005 | Albani ............ 424/450 |
| 2006/0147940 A1 | 7/2006 | Fodor |
| 2007/0148654 A1* | 6/2007 | Nakagawa ............ 435/6 |

OTHER PUBLICATIONS

Heer et al., Acceleration of incubation processes in DNA bio chips by magnetic particles. Journal of Magnetism and Magnetic Materials, 311, 244-248, 2007.*
Nagino et al., "Ultrasensitive DNA chip: gene expression profile analysis without RNA amplification," The Journal of Biochemistry, 139: 697-703 (2006).

* cited by examiner

*Primary Examiner* — Frank W Lu
(74) *Attorney, Agent, or Firm* — Alston & Bird LLP

(57) ABSTRACT

A method, device and system for hybridizing a target oligonucleotide to at least one array comprising a plurality of mixing beads are provided. A target solution is mixed by agitating the mixing beads while the target oligonucleotides are hybridizing to the complementary probes on the array. In another embodiment, a permeable barrier contains the mixing beads, thereby preventing them from contacting the array surface.

20 Claims, 12 Drawing Sheets

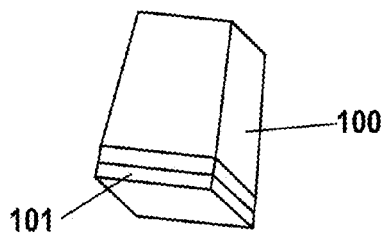
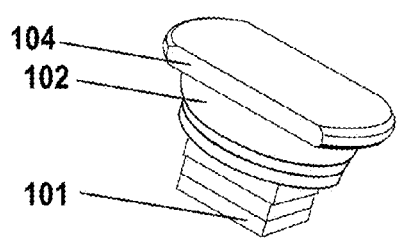
Fig.1A  Fig. 1B
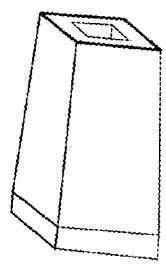
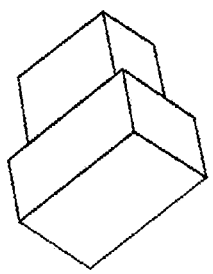
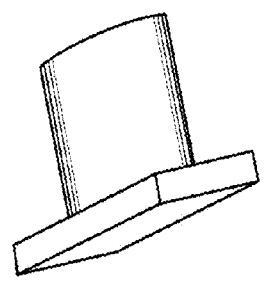
Fig. 2A  Fig. 2B  Fig. 2C

HYBRIDIZATION DEVICE, METHODS, AND SYSTEM USING MIXING BEADS

This application claims priority for provisional application 61/230,268, filed on Jul. 31, 2009.

FIELD OF INVENTION

One aspect of relates to sensors and sensor packages. More particularly, one aspect of the invention relates to the manufacturing and packaging of biological microarrays. In accordance with one aspect, processing methods and devices using mixing beads are provided for the fabrication of high density polymer arrays and assortments of high density arrays. In particular, one aspect relates to the devices, methods and systems for hybridizing a target oligonucleotide to a complementary probe on at least one array while mixing the target solution with mixing beads.

BACKGROUND OF THE INVENTION

Methods have been developed for producing high density microarrays. These microarrays have wide ranging applications and are of great importance to the pharmaceutical, biotechnology and medical industries.

Arrays of nucleic acid probes can be used to extract sequence information from nucleic acid samples. The samples are exposed to the probes under conditions that allow hybridization. The arrays are then scanned to determine to which probes the sample molecules have hybridized. One can obtain sequence information by selective tiling of the probes with particular sequences on the arrays, and using algorithms to compare patterns of hybridization and non-hybridization. This method is useful for sequencing nucleic acids. It is also useful in diagnostic screening for genetic diseases or for the presence of a particular pathogen or a strain of pathogen.

The field of nucleic acid assays has been transformed by microarrays which allow monitoring of gene expression events, expression profiling, diagnostic and genotyping analyses, among other applications. Substrates comprising arrays of probes (fragments of nucleic acids) need to be produced/manufactured in a manner that allows assays such as expression monitoring, genotyping and other studies to be performed accurately and efficiently. With more sensitive applications being contemplated for microarrays in the fields of pharmacogenomics and diagnostics, for example, there exists a need in the art for additional devices for manufacturing and processing of microarrays.

SUMMARY OF THE INVENTION

According to one aspect, a method, device and system are provided for hybridizing a target oligonucleotide to a complementary probe on at least one array. A first substrate including a support member with at least one array attached to a first end of the support member is provided. A second substrate including a container, such as a well, is also provided. A plurality of mixing beads is placed into the well of the second container. A solution with the target oligonucleotide is added to the well with the plurality of mixing beads. The first substrate is oriented above the second substrate such that an array attached to the first end of the support member on the first substrate can be dipped into the solution in the well of the second container. The mixing beads may be agitated while the array is being dipped into the solution. Thereby, the solution is being mixed by the beads while the target oligonucleotide is hybridizing to a complementary probe on the array.

Various alternatives, modifications and equivalents are possible. For example, certain methods, devices, and products are described herein using exemplary implementations for analyzing data from arrays of biological materials, in particular in relation to data from the Affymetrix® GeneTitan™ System. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

In another embodiment, an optional permeable barrier is provided. The permeable barrier contains the beads in a sub chamber of the container, preventing the mixing beads from directly contacting the array surface.

According to a further aspect, the mixing beads are magnetic and agitated to mix the target solution. In one embodiment, a magnetic field is applied to agitate the mixing beads in the target solution. In an alternate embodiment, a physical magnet is used to agitate the mixing beads to mix the target solution. In another embodiment, the support members are pegs and the substrate is a hybridization plate.

According to another embodiment, a plurality of encoded microparticles is attached to the end of the support member and the probes are attached to the microparticles. The above method is used to mix the target solution while the microparticles are dipped into the solution.

BRIEF DESCRIPTION OF THE DRAWINGS

The accompanying drawings, which are incorporated in and form a part of this specification, illustrate embodiments of the invention and, together with the description, serve to explain various aspects of the invention:

FIG. 1 illustrates examples of a sensor peg. FIG. 1A shows a sensor peg which is an assembly of the support member of FIG. 2A with a sensor. FIG. 1B depicts a sensor peg which includes an o-ring.

FIG. 2 illustrates various shapes of a support member. FIG. 2A shows a support member with tapered sides from narrow to wide wherein the sensor can be attached to the larger surface area. FIG. 2B illustrates a support member with a block post and a block platform in which the sensor can be attached to either end. FIG. 2C illustrates a support member with a cylindrical post and a square platform in which the sensor can be attached.

FIG. 3 illustrates a sensor cartridge designed for front-side scanning

FIG. 4 illustrates a sensor cartridge designed for back-side scanning

FIG. 6 illustrates a sensor strip with sensor pegs.

FIG. 7 illustrates a sensor strip with sensor cartridges.

FIG. 8 illustrates a sensor plate with at least one sensor strip.

FIG. 10 illustrates a hybridization plate.

FIG. 13 illustrates a wash plate.

FIG. 14 illustrates a detection plate.

FIG. 15 illustrates a package plate.

FIG. 17A shows a device comprising a permeable membrane containing the plurality of mixing beads in a sub chamber. FIG. 17B shows another device wherein the beads may be contained at the bottom of the well using an electromagnetic field.

DETAILED DESCRIPTION OF THE INVENTION

Figure 3A:
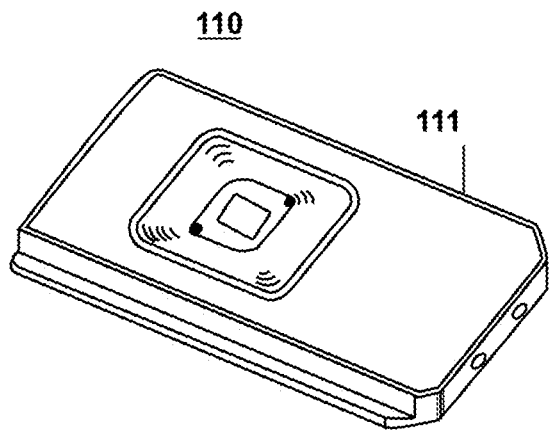
FIG. 3A shows the front view and FIG. 3B shows a cross section view of the sensor cartridge designed for front-side scanning.

Although the invention is described in conjunction with the exemplary embodiments, the invention is not limited to these embodiments. On the contrary, the invention encompasses alternatives, modifications and equivalents, which may be included within the spirit and scope of the invention. The invention has many embodiments and relies on many patents, applications and other references for details known to those of the art. Therefore, when a patent, application, website or other reference is cited or repeated below, the entire disclosure of the document cited is incorporated by reference in its entirety for all purposes as well as for the proposition that is recited. All documents, e.g., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. The term "an agent," for example, includes a plurality of agents, including mixtures thereof.

Throughout this disclosure, various aspects of this invention can be presented in a range format. When a description is provided in range format, this is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

The invention may employ arrays of probes on solid substrates in some embodiments. Methods and techniques applicable to polymer (including nucleic acid and protein) array synthesis have been described in, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in WO 99/36760 and WO 01/58593, which are all incorporated herein by reference in their entirety for all purposes. Patents that describe synthesis techniques include U.S. Pat. Nos. 5,412,087, 6,147,205, 6,262,216, 6,310,189, 5,889,165, and 5,959,098. Nucleic acid probe arrays are described in many of the above patents, but the same techniques are applied to polypeptide probe arrays.

Nucleic acid arrays that are useful in the invention include, but are not limited to, those that are commercially available from Affymetrix (Santa Clara, Calif.) under the brand name GeneChip® array. Example arrays are shown on the website at affymetrix.com.

Probe arrays have many uses including, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 (abandoned) and U.S. Pat. Nos. 5,856,092, 6,300, 063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

Samples can be processed by various methods before analysis. Prior to, or concurrent with, analysis a nucleic acid sample may be amplified by a variety of mechanisms, some of which may employ PCR. (See, for example, *PCR Technology: Principles and Applications for DNA Amplification*, Ed. H. A. Erlich, Freeman Press, NY, N.Y., 1992; *PCR Protocols: A Guide to Methods and Applications*, Eds. Innis, et al., Academic Press, San Diego, Calif., 1990; Mattila et al., *Nucleic Acids Res.,* 19:4967, 1991; Eckert et al., *PCR Methods and Applications,* 1:17, 1991; PCR, Eds. McPherson et al., IRL Press, Oxford, 1991; and U.S. Pat. Nos. 4,683,202, 4,683,195, 4,800,159 4,965,188, and 5,333,675, each of which is incorporated herein by reference in their entireties for all purposes. The sample may also be amplified on the probe array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics,* 4:560 (1989), Landegren et al., *Science,* 241:1077 (1988) and Barringer et al., *Gene,* 89:117 (1990)), transcription amplification (Kwoh et al., *Proc. Natl. Acad. Sci. USA,* 86:1173 (1989) and WO 88/10315), self-sustained sequence replication (Guatelli et al., *Proc. Nat. Acad. Sci. USA,* 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135 (abandoned).

Hybridization assay procedures and conditions vary depending on the application and are selected in accordance with known general binding methods, including those referred to in Maniatis et al., *Molecular Cloning: A Laboratory Manual*, 2$^{nd}$ Ed., Cold Spring Harbor, N.Y, (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874,219, 6,045,996, 6,386,749, and 6,391,623 each of which are incorporated herein by reference.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., or at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip® Mapping Assay Manual, 2004.

Hybridization signals can be detected by conventional methods, such as described by, e.g., U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676, allowed on Nov. 9, 2009) and PCT Application PCT/US99/06097 (published as WO 99/47964), each of which is hereby incorporated by reference in its entirety for all purposes).

The practice of the invention may also employ conventional biology methods, software and systems. Computer software products of the invention typically include, for instance, computer readable medium having computer-executable instructions for performing the logic steps of the method of the invention. Suitable computer readable medium include, for example a floppy disk, CD-ROM/DVD/DVD-ROM, hard-disk drive, flash memory, ROM/RAM, and magnetic tapes. The computer executable instructions may be written in a suitable computer language or combination of several computer languages. Basic computational biology methods which may be employed in the invention are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Ouelette and Bzevanis *Bioinformatics: A Practical Guide for Analysis of Gene and Proteins*, Wiley & Sons, Inc., 2$^{nd}$ ed., (2001). (See also, U.S. Pat. No. 6,420,108).

The invention can use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Genetic information obtained from analysis of sensors can be transferred over networks such as the internet, as disclosed in, for instance, (U.S. Patent Application Publication No. 20030097222), U.S. Patent Application Publication No. 20020183936, abandoned), U.S. Patent Application Publication No. 20030100995, U.S. Patent Application Publication No. 20030120432, 10/328,818 U.S. Patent Application Publication No. 20040002818, U.S. Patent Application Publication No. 20040126840, abandoned), Ser. No. 10/423,403 (U.S. Patent Application Publication No. 20040049354.

U.S. patent application Ser. Nos. 11/243,621, filed Oct. 4, 2005, 10/456,370, filed on Jun. 6, 2003 (now abandoned), and 61/267,738, filed on Dec. 8, 2009 describe different aspects of constructing sensor plates, sensor strip plates, processing plates or high-throughput (HT) plates, which may be useful in conjunction with the invention. Each of these applications is hereby incorporated by reference herein in their entirety for all purposes.

I. Definitions

The application refers to arrays of probes and arrays of sensors. A probe array is a plurality of probes attached to a surface of a substrate. Usually each different type of probe occupies a different area of the support and it is known or determinable, which of the different probes occupy different areas. There are usually multiple copies of the same probe within any one of the different areas. Probe arrays can be prepared by in situ synthesis on the substrate or by spotting of probes. Probe arrays can also be formed by distributing microparticles bearing probes to locations (e.g., indentations) of a support. ray (e.g., no more than 5, 2 or 1 cm$^2$) often characterized by a large number (e.g., at least 10$^2$, 10$^3$, 10$^4$, 10$^5$ or 10$^6$) of probes and/or high density of different probes (e.g., 10$^2$-10$^7$ per cm$^2$). The types of molecules in the probe array can be identical or different from each other. The probe array can assume a variety of formats, including, but not limited to, libraries of soluble molecules, and libraries of compounds tethered to resin beads, silica chips, or other solid supports. A probe array may include polymers of a given length having all possible monomer sequences made up of a specific set of monomers, or a specific subset of such a probe array. In other cases a probe array may be formed from inorganic materials (see Schultz et al., PCT application WO 96/11878).

The term "array" as used herein refers to an intentionally created collection of molecules which can be prepared either synthetically or biosynthetically. The molecules in the array can be identical or different from each other. The array can assume a variety of formats, including, but not limited to, libraries of soluble molecules, and libraries of compounds tethered to resin beads, silica chips, or other solid supports. An array may include polymers of a given length having all possible monomer sequences made up of a specific set of monomers, or a specific subset of such an array. In other cases an array may be formed from inorganic materials. (See, Schultz et al., PCT application WO 96/11878).

The term "array of sensors" refers to a systematic arrangement of sensors amenable to simultaneous analysis, usually in rows and columns. The sensors can be probe arrays, such as microarrays, or any types of sensor or probes described herein. An exemplary sensor array is a 12 sensor by 8 sensor array of microarrays, optionally with the individually microarrays being spaced as for the wells on a 96-well microtiter plate. An array of sensors may include any number of sensors, and if the sensors are probe arrays, the probe arrays can include any number of probes.

The term "detection plate" or "detection tray" as used herein refers to a body having at least two wells and at least one optically transparent window. A detection plate is a device used during the identification of the hybridization events on a plurality of sensors, such as from a sensor plate. Taking a sensor plate as an example, the corresponding detection plate is designed to receive the sensor plate. In one embodiment, the wells are filled with a solution such that the sensors from the sensor plate are submerged when the sensor plate and the detection plates are assembled. The scanning of the sensors is performed through the optically transparent window which can be made from a low-fluorescence material such as fused silica, or Zeonor (Nionex). Optionally, a detection plate can have a physical barrier resistant to the passage of liquids around the individual wells or around a plurality of wells.

The term "monomer" as used herein refers to any member of the set of molecules that can be joined together to form an oligomer or polymer. The set of monomers useful in the invention includes nucleotides and nucleosides for nucleic acid synthesis and the set of L-amino acids, D-amino acids, or synthetic amino acids for polypeptide synthesis. Different basis sets of monomers may be used at successive steps in the synthesis of a polymer.

The term "nucleic acid" as used herein refers to a polymeric form of nucleotides of any length, either ribonucleotides, deoxyribonucleotides or peptide nucleic acids (PNAs) or (Locked nucleic acids, LNAs), that include purine and pyrimidine bases, or other natural, chemically or biochemically modified, non-natural, or derivatized nucleotide bases. Nucleic acids can be single or double stranded. The backbone of the nucleic acid can include sugars and phosphate groups, as may typically be found in RNA or DNA, or modified or substituted sugar or phosphate groups. A nucleic acid may include modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids can be isolated from natural sources, recombinantly produced or artificially synthesized and mimetics thereof, such as LNA, "Locked nucleic acid". A further example of a nucleic acid is a peptide nucleic acid (PNA). Double stranded nucleic acid usually pair by Watson-Crick pairing but can also pair by Hoogsteen base pairing which has been identified in certain tRNA molecules and postulated to exist in a triple helix. The term "oligonucleotide" refers to a nucleic acid of about 7-100 bases, (e.g., 10-50 or 15-25).

A probe has specific affinity for a target (or analyte) in a sample. For nucleic acid probes and nucleic acid targets, specific affinity is primarily determined by ability to form Watson Crick complementary base pairs on hybridization. For example, an oligonucleotide probe can be designed to be perfectly complementary to its intended target. Targets may be naturally-occurring or man-made molecules. Also, they can be employed in their unaltered state or as aggregates with other species. Targets may be attached, covalently or noncovalently, to a binding member, either directly or via a specific binding substance. Examples of targets include antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. U.S. Pat. No. 6,582,908 provides an example of probe arrays having all possible combinations of nucleic acid-based probes having a length of 10 bases, and 12 bases or more. Nucleic acid probes can be, for example, olignucleotides or cDNAs. Probes can be linear. A probe may also consist of an open circle molecule, comprising a nucleic acid having left and right arms whose sequences are complementary to the target, and separated by a linker region (see, e.g., U.S. Pat. No. 6,858,412, and Hardenbol et al., Nat. Biotechnol., 21(6):673 (2003)). A probe, such as a nucleic acid can be attached directly to a support (optionally drivatized with a linker). A probe can also be attached to a microparticle, and the microparticle attached to the support, for example, in an indentation or divot in the support. Examples of encoded microparticles, methods of making the same, methods for fabricating the microparticles, methods and systems for detecting microparticles, and the methods and systems for using microparticles are described in U.S. Patent Application Publication Nos. 20080038559, 20070148599, and PCT Application No. WO 2007/081410 (all incorporated by reference). Such microparticles are preferably encoded such that the identity of a probe borne by a microparticle can be read from a distinguishable code. The code can be in the form of a tag, which may itself be a probe, such as an oligonucleotide, a detectable label, such as a fluorophore, or embedded in the microparticle, for example, as a bar code. Microparticles bearing different probes have different codes. Microparticles are typically distributed on a support by a sorting process in which a collection of microparticles are placed on the support and the microparticles distribute to areas of the support. The areas can be defined by indentations, by sticky patches among other methods. A "Probe Target Pair" is formed when two macromolecules have combined through molecular recognition to form a complex.

The term "sensor" as used herein refers to any device that detects or analyzes an analyte or target in a sample. The sensor includes a recognition element or probe, e.g. enzyme, receptor, molecule, nucleic acid, antibody, or microorganism typically attached to a substrate. A sensor may be associated with an electrochemical, optical, thermal, or acoustic signal transducer that on binding of the probes permits analysis and or detection of chemical properties or quantities of an analyte, or can in combination with a target, result in a signal, detectable by a separate reader. A sensor can be a probe array, such as a microarray with any number of probes attached to a support.

The term "sensor plate" as used herein refers to a plate having one or more sensors, although typically the sensor plate includes a plurality of sensors. The sensor plate can be referred to by a name based on the type of sensor. For example, if the sensors on a sensor plate are microarrays, then the plate can be referred to as a microarray plate, DNA plate, or an oligonucleotide plate.

The term "shipping plate" as used herein refers to a device with at least two wells suitable for protecting at least two sensors. The shipping plate is a device used during the handling and shipping of the sensors, such as on a sensor plate. The shipping plate is designed to receive the sensor plate. Once the sensor plate is assembled and inspected, the shipping plate is assembled, contacted, or connected with the sensor plate. Optionally, the shipping plate can have a physical barrier resistant to the passage of liquids and gases around the individual wells or around a plurality of wells. Optionally, the shipping plate may include features to allow multiple sensor plates to be stacked on top of each other.

The term substrate refers to a material or group of materials having a rigid, semi-rigid surface or flexible surface suitable for attaching an array of probes. In one embodiment, the surface may be a combination of materials where at least one layer is flexible. Surfaces on the solid substrate can be of the same material as the substrate. In another embodiment, the substrate may be fabricated form a single material or be fabricated of two or more materials. Thus, the surface may be composed of any of a wide variety of materials, for example, polymers, plastics, resins, polysaccharides, silica or silica-based materials, carbon, metals, inorganic glasses, membranes, or any of the above-listed substrate materials. In a further embodiment, the surface can be supported by a flexible material or a solid material. In many embodiments, at least one surface of the substrate is flat, although in some embodiments it may be desirable to physically separate synthesis regions for different compounds with, for example, wells, raised regions, pins, etched trenches, or the like. According to other embodiments, the substrate takes the form of beads, resins, gels, microspheres, or other geometric configurations. (See, U.S. Pat. No. 5,744,305 for exemplary substrate, which is hereby incorporated by reference herein in its entirety for all purpose).

The term "stain plate" as used herein refers to a device with at least two wells suitable for staining of a sensor plate. In one embodiment, the well depth is optimized to use the minimum volume of sample that is desired. The stain plate is a device used during an assay of the sensor, in particular the staining step for a plurality of sensors, such as on a sensor plate. Taking the sensor plate as an example, the corresponding stain plate is designed to receive the sensor plate. In one embodiment, after the stain solution is deposited into the wells of the stain plate, the sensor plate is assembled with the stain plate such that the active surfaces of the sensors are submerged into the stain solution. Optionally, the stain plate may include a physical barrier resistant to the passage of liquids and gases around the individual wells or around a plurality of wells.

The term "support member" and "peg" as used herein are used interchangeably and refer to a "support" that projects a material of interest from a surface which the peg can be attached. The peg can be made of various materials and can take on various forms as described above.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "wafer" as used herein refers to a substrate having a surface to which a plurality of probe arrays (e.g., microarrays) are bound. The substrate can have a flat surface of glass or silica among other materials. Surfaces on the solid substrate can be formed from the same material as the substrate or a different material. Thus, the surface can be any of a wide variety of materials, for example, polymers, plastics, resins, polysaccharides, silica or silica-based materials, carbon, metals, inorganic glasses, membranes, or any of the above-listed substrate materials which may also be present in combinations or layers. In one embodiment, the surface may be optically transparent and may have surface silicon hydroxide functionalities, such as those found on silica surfaces.

The term "wash plate" as used herein refers to a device with at least two wells suitable for washing a sensor. The well depth and design can be optimized to efficiently wash the sensor with an optimal volume. The wash plate is a device used during an assay of the sensors, in particular the washing step for a plurality of sensors, such as on a sensor plate. Taking the sensor plate as an example, the corresponding wash plate is designed to receive the sensor plate. In one embodiment, after the washing solution is deposited into the wells of the wash plate, the sensor plate is assembled. The active surfaces of the sensors are submerged into the washing solution. Optionally, the wash plate may have a physical barrier resistant to the passage of liquids and gases around the individual wells or around a plurality of wells.

II. Specific Embodiments

The invention provides methods and components for assembly and processing of sensors. The assembled sensors with a support are sometimes referred to as a sensor peg. The sensor peg can readily be assembled in different ways and combinations thereby allowing many different sensor pegs to be assembled into various devices, such as, for example, cartridges, modules (i.e. strips) and plates. Such sensor peg assemblies offer advantages of requiring low volume of reagents (i.e. target) for a user. The projected sensor can be placed into a well such that a minimum amount of reagent is required to react with the surface of the sensor.

The sensor pegs are particularly useful for sensors that are probe arrays, for example, a microarray of nucleic acid probes, such as the GENECHIP® array. Such probe arrays have a variety of applications in analyzing samples, for example, in expression monitoring, detecting mutations, or detecting presence of analyte. In some experiments, a user may wish to mix the solution while submerging the sensor in the solution. According to an embodiment, a method, device and system are provided for processing sensors on the sensor pegs by using a method to mix the solution comprising a plurality of mixing beads in the wells during a reaction step. Processing steps typically include contacting individual sensors with individual samples, hybridization, washing, staining and scanning. Some or all of these steps can be performed in a largely or completely automated fashion using equipment such as the GENETITAN™ or GENEATLAS™ instruments.

Sensor Packages Having Sensor Pegs

The following describes the exemplary design, materials, manufacturing processes and application protocols used for processing a sensor peg as an illustration of the various aspects of the invention.

Sensor Peg

In the exemplary embodiment, the sensor peg (103) as depicted in FIGS. 1A and 1B includes a support member (100) wherein the support member has at least one sensor (101) and is attached to an end of the support member. A support member can be formed as part of the holding device by machining, molding, and the like. A support member can also be formed separately and then attached by fasteners, bonding, ultrasonic welding, and the like. A support member material can be made from any material that is compatible with the chemical reactants, other operating environment (such as temperature) and solvents that are placed in the wells. The material of a support member can be different than the material of the sensor. Any of a variety of organic or inorganic materials or combinations thereof, may be employed for a support member including, for example, metal, plastics, such as polypropylene, polystyrene, polyvinyl chloride, polycarbonate, polysulfone, etc.; nylon; PTFE; ceramic; silicon; (fused) silica, quartz or glass, and the like. A support member may be solid, semi-rigid, flexible or a combination thereof and be of any shape. The shape of a support member may be, for example, rectangular, diamond, square, circular, oval, any modifications thereof and so forth. Examples of different shaped support members (100) are shown in FIGS. 2A-2C. A support member (100) can be solid or hollow or partially hollow and the sensor can be attached at either end of the support member. The shape and size of one end of a support member (100) where a sensor is attached can be similar to that of the sensor. By way of illustration and not limitation, the dimensions of a support member (100) are about 0.5 mm to about 15 mm in length, width and depth.

In another embodiment, pegs (100) are designed and assembled to allow a plurality of sensors to be processed at one time. The dimensions of a peg can depend on several factors, such as, the size of the sensor, the number of sensors to be processed at one time and the method and apparatus used for further processing.

The formation of unwanted bubbles may appear when the sensor is submerged into its corresponding well containing array reactants in solution. There are several ways in which bubbles can be created. For example, bubbles can be created during an insertion of a sensor peg into a well. Bubbles may also appear while a liquid is introduced into a well. In some cases, a heat source is applied to provide an appropriate hybridization temperature. Heating of the sample may also create bubbles in the solution in the well. There are several ways to prevent the formation of bubbles, i.e. degassing of the solution, redesign of the receiving chamber, hydrophobic/hydrophilic coatings, design of the wells, design of the support member, mixing, etc.

In one aspect, a method to reduce bubbles is provided which includes modifying the structure of the support member. A support member with sloped side walls are provided to reduce bubbles in a liquid sample during contact with the sensor and mixing of a liquid sample. In one embodiment, the support member is sloped such that the top is narrow and then widens at the bottom of the support member where the sensor is attached, see FIG. 1A. This may allow sufficient volume for gas to expand such that the bubbles diffuse at the surface of the liquid.

The methods and apparatus are suitable for various types of sensors, such sensors may include "nucleic acid sensors" such as nucleic acid microarrays. In one embodiment, the sensor can be a microarray such as a cDNA array, a peptide array, a bead array or an in situ synthesized high density oligonucleotide array. The microarrays can include a substrate. In another embodiment the substrate is a flat glass or silica. Surfaces on the solid substrate may be composed of the same material as the substrate or a different material. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface SI-OH functionalities, such as those found on silica surfaces. The sensor peg can further include a sensor wherein the sensor is a microarray. In one embodiment, a microarray peg (103) is provided wherein the support member (100) has sloped walls as mentioned in the previous section to assist in eliminating bubbles and where the end of the support member is shaped as a square to fit the sensor which is a micoarray (101) as shown in FIG. 1A. In another embodiment, a microarray peg (103) is provided wherein the support member includes a component which assists in the seal during a hybridization process, for example, an o-ring (102). In one aspect, a micoarray peg (103) is provided wherein the support member includes a component to assist in the depth at which the sensor is placed into solution, for example a ledge (104) as illustrated in FIG. 1B.

According to an alternate embodiment, a plurality of arrays, such as beads, microparticles, etc. are attached to the first end of the support member. In one embodiment, a plurality of miniaturized microparticles are attached to the end of the support member. (See U.S. patent application Ser. No. 11/521,057, filed Sep. 13, 2006, now U.S. Pat. No. 7,745,091 B2, for details regarding miniaturized microparticles, which is incorporated by reference it its entirety). There are a wide variety of known methods of attaching particles, such as beads and microparticles, to solid supports. In another embodiment, the miniaturized microparticles are magnetic and attached to the support member by applying a magnetic field. It is also understood by any person skilled in the art that there are no limitations as to the type of magnetic field that can be applied, for example, paramagnetic, ferromagnetic, etc.

Sensor Cartridge

Figure 3B:
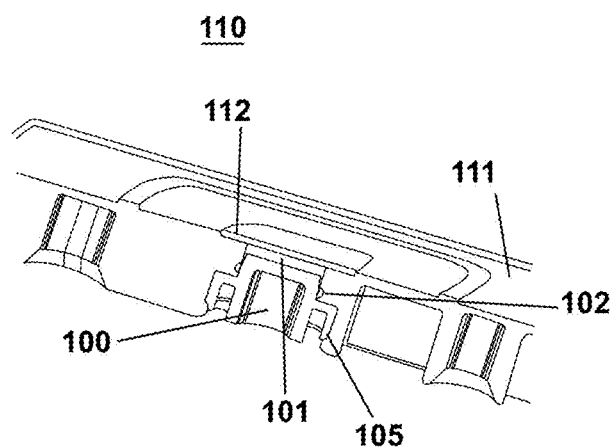

According to one aspect, a sensor cartridge (110) as depicted in FIGS. 3A and 3B, includes a housing (111) wherein the housing contains at least one sensor peg (103). In one embodiment, the sensor cartridge further includes a sensor (101) wherein the sensor is a microarray which is attached to the end of the support member (100). In another embodiment, the sensor peg includes a sealing mechanism (102) or a physical barrier resistant to the passage of liquids. One example of a physical barrier can be in a form of a gasket or any of a wide variety of seals to prevent the escape of a gas or fluid. In another embodiment, the sensor peg includes a snapping mechanism. A snapping mechanism can include a variety of assembly methods that assembles components together. An example of a snapping mechanism is shown in FIG. 3B, where a part of the peg (105) is used to snap the sensor peg into place in the cartridge.

In one embodiment, two or more different types of scanning methods, for example, a front-side scanning, a back-side scanning, etc. may be used to scan a sensor in the sensor cartridge, for example an array cartridge. The array cartridge may contain buffer while the array is scanned. Front-side scanning is, for example, when the scanning is performed through the active surface of the array. Back-side scanning, on the other hand, is where the scan may be performed from the back of the array. In general, the array is made from a transparent substrate, such that the scanner can scan through the substrate. An example of a sensor cartridge which utilizes front-side scanning is shown in FIGS. 3A and 3B. A piece of transparent material (112) (for example, plastic, glass, etc.) is used to contain the buffer and provide a mechanism to scan the probes on the array. FIG. 3B shows the sensor peg indicated by the sensor (101) and the support member (100) within the housing (111). The active area of the sensor is facing out from the support member and into the chamber of the cartridge which contains a window (112). The scanning can be performed through the window while the buffer is contained within the cartridge. This type of sensor cartridge can utilize the maximum surface area of the sensor for scanning since the surface of the active area of the sensor can be fully exposed.

Figure 4A:
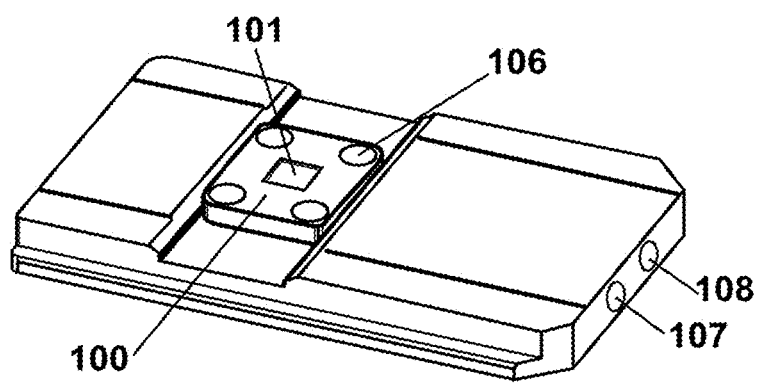
FIG. 4A shows the front view and FIG. 4B shows a cross section view of the sensor cartridge designed for back-side scanning.
Figure 4B:
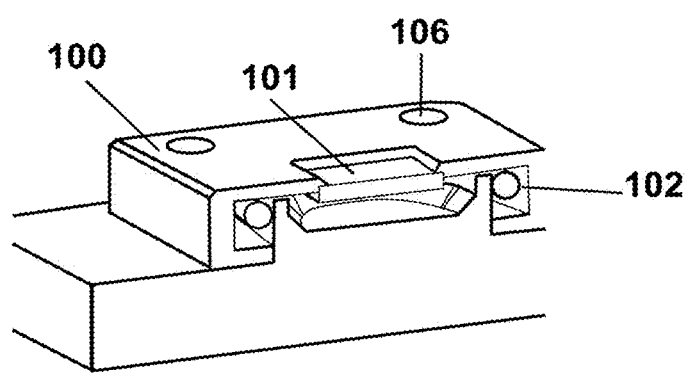

In an embodiment, the sensor cartridge includes a sensor (101) attached to the end of a support member (100), having the active side facing down onto the support member (FIG. 4A). In this configuration, the wall of the support member can form a space to contain a liquid (FIG. 4B). The back-side scanning configuration can be more suitable for larger sensors since the information scanned will be dependent on the surface area used to mount the sensor. In another embodiment, the support member is hollow and the active side of the sensor is facing down into the support member where the walls and the sensor create a well in which liquid can be contained. In this example, a separate window is not necessary since the scanning is performed from the back of the sensor. In one aspect, the sensor peg can be assembled into a cartridge by welding, adhesive, screws, or other attaching methods. In one embodiment the support member includes countersink holes (106) for screws to assemble the support member onto the cartridge as shown in FIGS. 4A and 4B. In this example, the support member also includes an o-ring (102).

According to one aspect, the inlet (107) and outlet (108) ports can be on any of the sides of the cartridge: front, back or any of the other sides. One example, of the location of the inlet (107) and outlet (108) is shown in FIG. 4A.

Experiments were performed to show that the hybridization intensity results of the scanned microarrays from a sensor cartridge with a sensor peg were comparable to those results from a standard embodiment of a biological probe array that may for example include what is generally referred to as a GENECHIP® probe array.

Sensor Array Plate

In the exemplary embodiment, the sensor array plates 200 allow a plurality of sensors 101 to be processed simultaneously in an assay process of an HT analyzer, such as the GENETITAN™ instrument. The dimensions of sensor plate 200 may vary depending on the size and number of the sensors 101, and the processing methods and apparatus.

Figure 5:
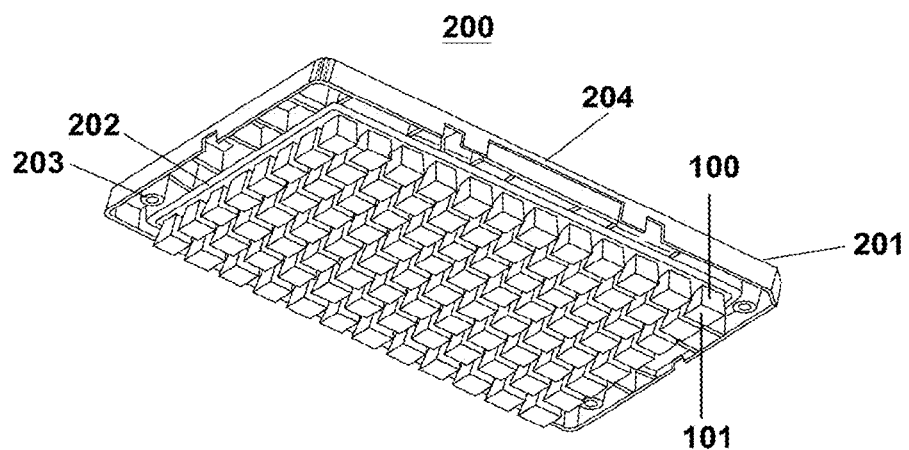
FIG. 5 illustrates a microarray plate with a plurality of microarray pegs.

In an exemplary embodiment, illustrated in FIG. 5, the sensor plate 200 includes a holding device (201) wherein the holding device has a plurality of support members (100) which can be, for example, pegs projecting from one side of the holding device (i.e. 96 pegs). In one embodiment, the sensor plate further includes a plurality of sensors (101) wherein the sensors are microarrays attached to the end of the support members (100). The support members can be part of the holding device or be separate parts assembled onto the holding device. In an alternative embodiment, the sensors are attached directly onto the holding device without support members. The attachment method can be comprised of a low-fluorescence adhesive, welding or other attaching methods. In another embodiment of the application, the sensors, such as microarrays, can be attached to a surface of the support members which can be substantially flat with regard to the surface of the support member. The attachment of the sensors to the supporting members can be performed before or after the support members are attached to the holding device. The array plate can be made of any material which can withstand high temperatures for hybridization and can be stored in cold temperatures for storage (i.e. cyrolite, Hi-Lo acrylic, etc.). In a further embodiment, the sensor plate includes a sealing surface such as an elastomeric seal (202), alignment features (203) and a clamping feature (204). An advantage of having an elastomeric seal as part of the sensor plate is not having to have an elastomeric seal on multiple mating plates (for example, hybridization plate, shipping plate, reagent plate, detection plate, packaging plate, etc.). In another embodiment, the elastomeric seal is a gasket.

A holding device material can be made from any material that is compatible with the chemical reactants and solvents that are placed in the wells. Any of a variety of organic or inorganic materials or combinations thereof, may be employed for the holding device including, for example, metal, plastics, such as polypropylene, polystyrene, polyvinyl chloride, polycarbonate, polysulfone, etc.; nylon; PTFE, ceramic; silicon; (fused) silica, quartz or glass, and the like. In one embodiment, the material of the holding device is transparent. The holding device (201) may be of any shape. The shape of the holding device can take on various forms, for example, a rectangular, square, circular, oval, and so forth. The dimensions of the holding device can be sufficient to allow for a desired number of support members and sensors of a predetermined size to be incorporated onto the holding device. The holding device can be formed by machining, molding, mechanical forming, and the like. The dimensions of the holding device can be about 10 mm to about 400 mm in length, about 10 mm to about 400 mm in width, and about 0.25 mm to about 25 mm in depth.

In a circumstance where the reaction requires high hybridization temperature and cold temperature storage, the holding device can be made of any material which can withstand high temperatures for hybridization and be stored in cold temperatures for storage (i.e. cyrolite, Hi-Lo acrylic, polycarbonate, etc.).

In one embodiment, the sensor plate (200) includes a holding device (201) and a plurality of sensor pegs (103), wherein the sensor pegs are described above. The holding device (201) and the support members (100) can be manufactured from a single injected mold. The microarrays are then attached to the support members to create an array plate.

In another embodiment, a sensor plate (200) is created by attaching a plurality of sensor pegs to a holding device. An example of a holding device is shown in FIG. 5 where the surface on which the sensor pegs are supported is flat. The advantages of having a system with a holding device and separate sensor pegs are: (1) manufacturing flexibility, (2) in-process inspection, (3) possible additional venting space to eliminate bubble formation, and (4) various peg profile designs.

In one aspect, array pegs are attached to the holding device. First, a sensor peg is assembled by bonding a microarray to a support member. A low-fluorescence adhesive at the working emission wavelengths of the hybridized, labeled probe arrays can be used to bond the back surface of the microarray to the top surface of the peg such that the probes on the microarray are not damaged. In one embodiment, the curing process can be performed through the top surface of the microarray, from the side, or a combination thereof to bond the microarray to the support member.

In another embodiment, the holding device material is transparent such that the adhesive connecting the sensor peg to the plate can be light cured from the bottom, through the holding device. In a particularly embodiment the material of the holding device is a plastic, Lexan HPI, which is a transparent material that can allow the sensor plate to withstand high temperatures for hybridization, and cold temperatures for storage.

The holding device of the sensor plate or sensor cartridge can be designed such that various sizes of sensors (101) on the support members can be attached. The design of the holding device can also be customized to fit various sizes of sensors. In some embodiments, the holding device can be made of an optically clear/transparent material such that the transparency characteristic can assist in the manufacturing of the sensor plate. The support members can also be made of a dark, light absorbing material to minimize the fluorescence background during scanning The transparency of the HT plate facilitates the determination of a sample being present.

According to one aspect, a method is provided for constructing a sensor plate. A plurality of sensors is produced by dicing a substrate. Plates and support members having a first end and a second end are provided. First, a sensor from the diced substrate is attached to the first end of a support member. Next, the second end of the support member is attached to a plate. These steps are repeated until the desired sensor plate is produced. In one embodiment, the sensors are microarrays and the support members are pegs.

In one embodiment, the method further includes the attaching steps as bonding steps using a curable low fluorescence adhesive. According to another, the adhesive is cured with a solid state narrow wavelength light source. In another embodiment, the light source is a blue LED. The LED's wavelength can be from 430 nm to 480 nm, or the wavelength can be approximately 455 nm.

Sensor Strip

Figure 6A:
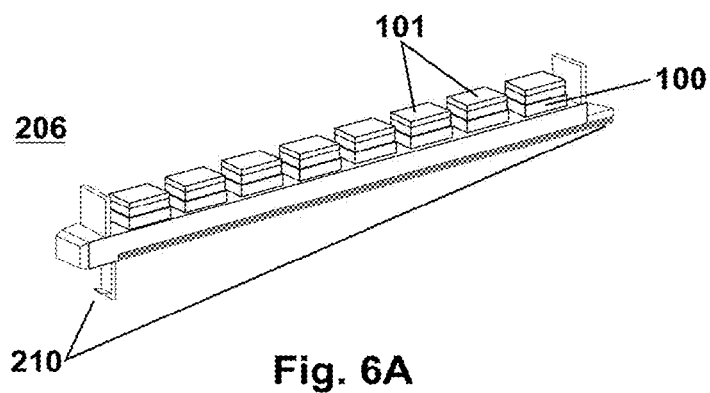
FIG. 6A shows an uncovered sensor strip and FIG. 6B shows a covered sensor strip with sensor pegs.
Figure 6B:
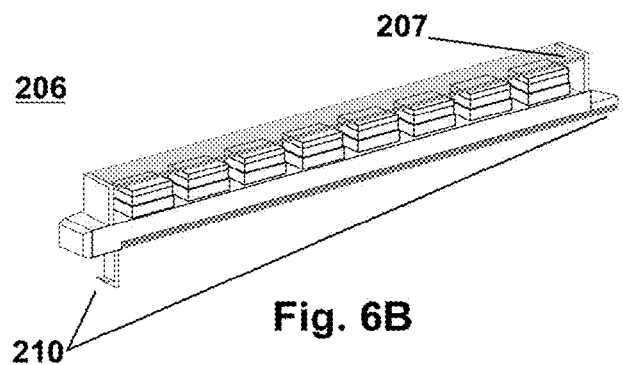

A sensor strip (206), as depicted in FIGS. 6A and 6B, includes a plurality of sensors (101), for example, at least 4, 8, 12, 96 sensors (101) where the sensors may be arranged in a row. In one embodiment, a sensor strip can include a plurality of sensor pegs. The number of sensors on a sensor strip can be from 8 to 12 sensors. To allow for sensor strip consumption flexibility, a gasket can be incorporated into a sensor strip. The sensor strip can also include a cover (207) as shown in FIG. 6B.

Figure 7A:
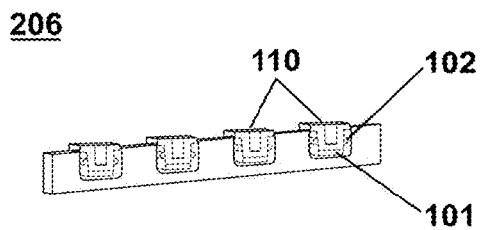
FIG. 7A shows an uncovered sensor strip and FIG. 7B shows a covered sensor strip with sensor cartridges.
Figure 7B:
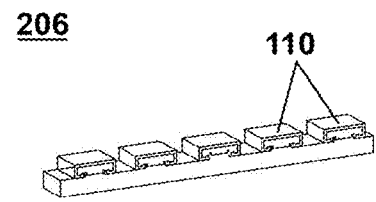

In another embodiment, the sensor strip (206) can also include a plurality of sensor cartridges (110). FIG. 7A shows a cross sectional view of a sensor strip of front-side scanning sensor cartridges (refer to FIG. 3B for details of the sensor peg) and FIG. 7B indicates a cross sectional view of a sensor strip of back-side scanning sensor cartridges (refer to FIG. 4B for details of the sensor peg).

Figure 8A:
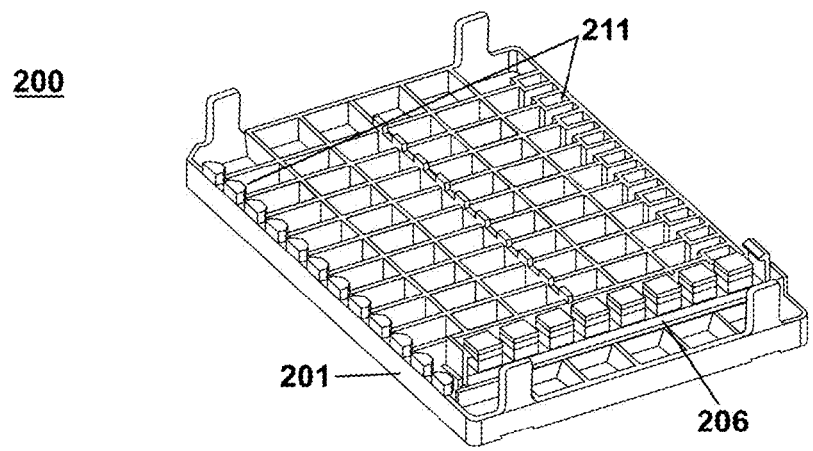
FIG. 8A shows a sensor plate with one sensor strip and FIG. 8B shows a full sensor plate with one cover off of one sensor strip.
Figure 8B:
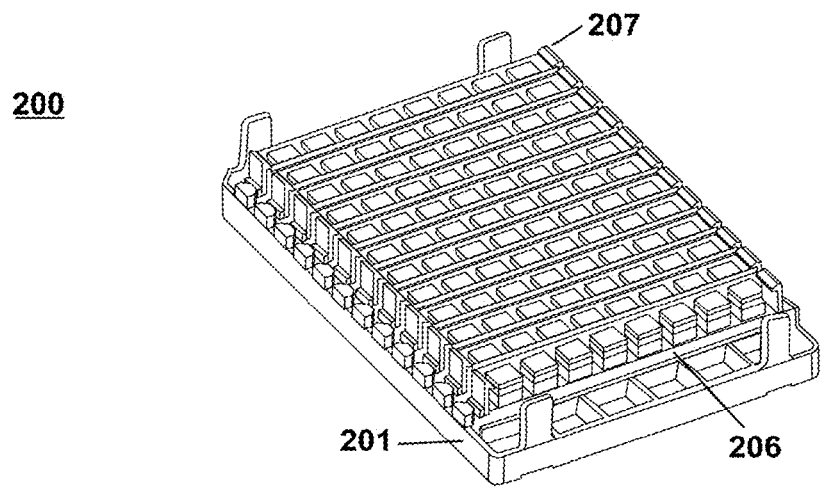

In another embodiment, the sensor plate (200) can be a holding device with a plurality of sensor cartridges. Sensor strips can be assembled onto a holding device (201) to combine a plurality of sensor strips to form a sensor plate. The sensor strip includes a plurality of sensor cartridges. According to one aspect, a sensor strip can be assembled via snaps or latches (211). There can be attaching mechanisms to attach a sensor strip to another component as shown in FIGS. 6A and 6B. These attaching mechanisms can be any type of method to attach one part to another. For example, a latching mechanism (210) as shown in FIGS. 6A and 6B can be used to attach the sensor strip in FIG. 6A to the holding plate (201) in FIG. 8A by connecting to the mating parts (211). In this example, a part at one end of the sensor strip can be fitted into the mating part while a hook at the other end of the sensor strip is pressed into the mating part and locks into place. In addition, the attaching mechanism can include a feature that assists in aligning the part into the mating part (see indentation in the mid section between mating parts (211) in FIG. 8A. FIG. 8A shows a holding device (201) with one sensor strip (206) of 8 sensor pegs attached. The user of the sensor plate has the option of processing one or more sensor strip at a time. FIG. 8B shows a sensor plate of a plurality of covered sensor strips (206) with one strip exposed. A cover (207) can protect the sensors from contamination while the other sensors are being processed.

HT Plates

In another aspect, the system for processing array plates includes various other plates such as a hybridization plate, washing plate, staining plate, detection plate, reagent plate and packaging plate. The number of wells in an HT plate can be at least as great as the number of sensors to be tested on the sensor plate. The wells are generally coplanar with the surface of the holding device in which the well openings are arranged. The planar openings of the wells may be of any shape such as, for example, rectangular, square, circular, oval, elliptical, rectangular or square with rounded corners and so forth. The bottom of the wells may be level, conical, or slanted as discussed more fully herein. The planar dimensions of the opening of the wells are dependent on the planar dimensions of the sensor aligned with the well opening. The planar dimensions of the well openings can be about 0.5 mm to about 40 mm in length and about 0.5 mm to about 40 mm in width, or can be about 1 mm to about 30 mm in length and about 1 mm to about 30 mm in width. By way of illustration and not limitation, some examples of typical planar dimensions for length and width are about 23 mm by about 54 mm, about 23 mm by about 29 mm, about 6 mm by about 23 mm, about 10 mm by about 13 mm. The volume capacity of the wells can be about 100 ml to about 300 ml, or can be about 1 ml to about 100 ml. In one embodiment, the holding device with the wells is similar to a standard microtiter plate, which is used for high throughput analysis, such as, for example a 24-, 96-, 256-, 384-864- or 1536-well plate.

HT Assembly

The assembly and removal of the sensor plate to the hybridization plate may be performed with a mechanical device. The holding device may have a feature along the border that facilitates the connection to a HT plate, for example, a latching or unlatching mechanism.

It is desirable to have a seal between the perimeter of the surface of the support member connected to the sensor and the surface of the holding device of the wells comprising the well openings. Various approaches may be employed. In one approach, a flexible member can be utilized to form the seal. The flexible member can be a gasket and the cross sectional shape of the gasket may be, for example, rectangular, or square with straight sides and a flat, concave or convex bottom, and the like. The flexible member can be, for example, made of elastomer, rubber, flexible plastic, flexible resins, and the like and combinations thereof. The thickness of the gasket is not a problem and there is no deleterious effect on the liquid samples from the flexible member material. In any event the flexible material should be substantially inert with respect to the liquid samples in the wells. The dimensions of the gasket can be 1 mm to about 5 mm deep and about 1 mm to 5 mm wide, or can be about 3 mm deep and about 3 mm wide.

There are several ways to form a seal with a gasket between the sensor plate and the hybridization plate such that the sample does not evaporate and mix between the wells. The gasket can be part of the sensor plate, the HT plate or a separate piece like a clam shell device. The gasket can be formed around each well; however this will require a certain thickness around each well to contain the gasket. Experiments were performed to verify that the samples in the wells would not mix with each other if the gasket was formed around a plurality of wells. The clamping mechanism can be with screws, latches, or other type of clamping mechanism.

Hybridization Plate

Figure 9:
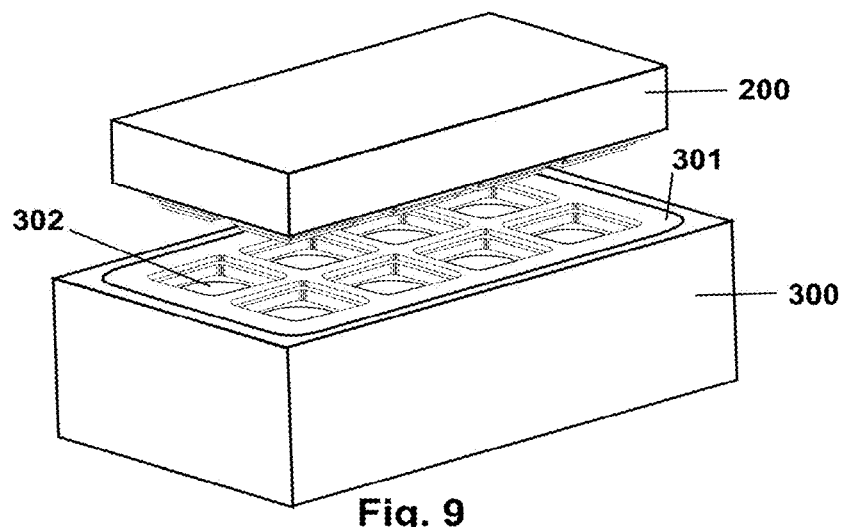
FIG. 9 illustrates a hybridization assembly.

According to one aspect, a hybridization plate (300), as depicted in FIG. 9, includes a sealing surface (301) such as an elastomeric seal between the sensor plate (200) and the hybridization wells (302) when the hybridization plate and a sensor plate are assembled for the hybridization process to create the hermetic seal necessary for high temperature incubation. The sealing surface (301) can be made of any material known in the art, such as, an elastomeric over-mold seal. This seal may facilitate the separation of the sensor plate from the hybridization plate. The wells of the hybridization play and the support members of the sensor plate can be designed to reduce the hybridization target volumes, thus minimizing the cost for processing the sensors on the sensor plates. A hybridization plate (300) can include a plurality of wells (302), for example, at least 2, 4, 8, 12, 96 wells where the wells may be arranged in a row or a matrix. The shape of the hybridization plate may be, for example, rectangular, square, diamond, circular, oval, and so forth. The dimensions of the hybridization plate can be designed such that a desired number of wells of predetermined size can be incorporated into the holding device. The wells can be formed in the holding device by, for example, machining, mechanical forming, molding, embossing, stamping and the like. The dimensions of the holding device can be about 2.54 cm (1") to about 12.7 cm (5") in length, about 2.54 cm (1") to about 8.89 cm (3.5") in width, and about 0.63 cm (0.25") to about 1.27 cm (0.5") in depth. By way of illustration and not limitation, an example of typical approximate dimensions for length and width of substrates, is about 12.7 cm (5")×about 12.7 cm (5").

Figure 10A:
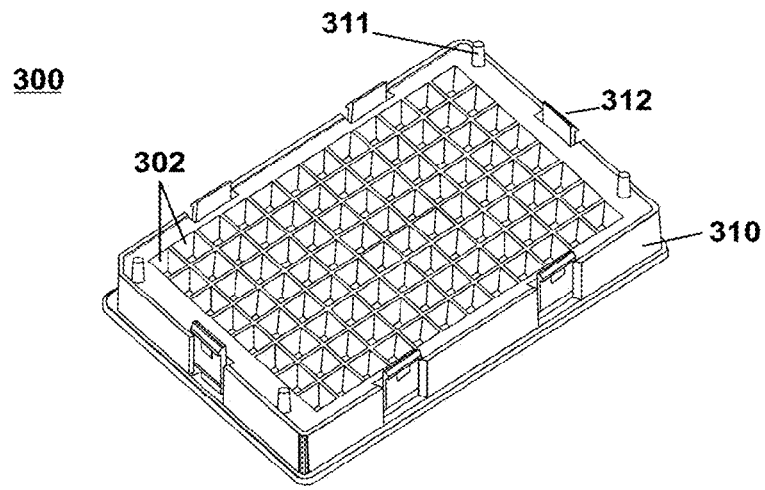
FIG. 10A shows a top view and FIG. 10B shows a bottom view of the hybridization plate.
Figure 10B:
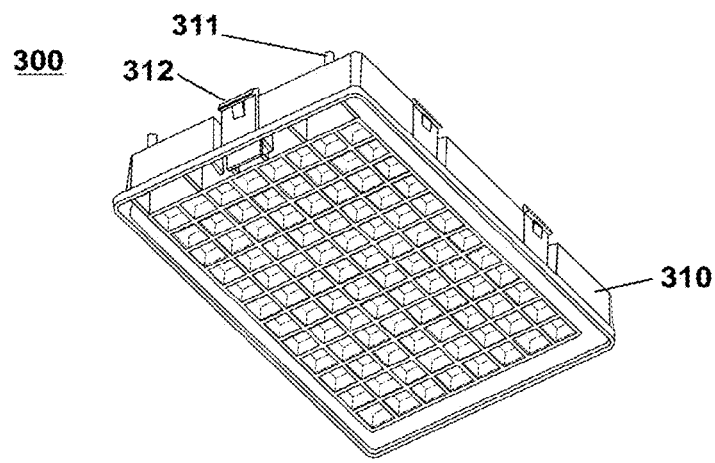

In a further embodiment, a hybridization plate (300) can be designed to minimize the fluidic volume introduced into the hybridization well, as depicted in FIGS. 10A and 10B. The spacing between the bottom of the well and the surface of the array, when the array plate is assembled, can be minimized. In one embodiment, the hybridization plate is a plate (310) with a plurality of wells (302) that has alignment features (311) and clamping features (312) along the borders of the plate. These features assist in the assembling and clamping the array plate to the hybridization plate. The hybridization plate can be made from any material that is compatible with the chemical reactants and solvents that are placed in the wells and can sustain high temperatures such as a high temperature molded plastic material (i.e. polycarbonate, polypropylene, etc.). In one embodiment, the hybridization plate is made out of Lexan HPI which is chemically resistant and allows the hybridization plate to withstand high temperatures for hybridization, and cold temperatures for storage. This material enables hybridization conditions at temperatures in excess of 60° C. In a further embodiment, the hybridization plate is suitable for chemiluminescence.

Figure 11:
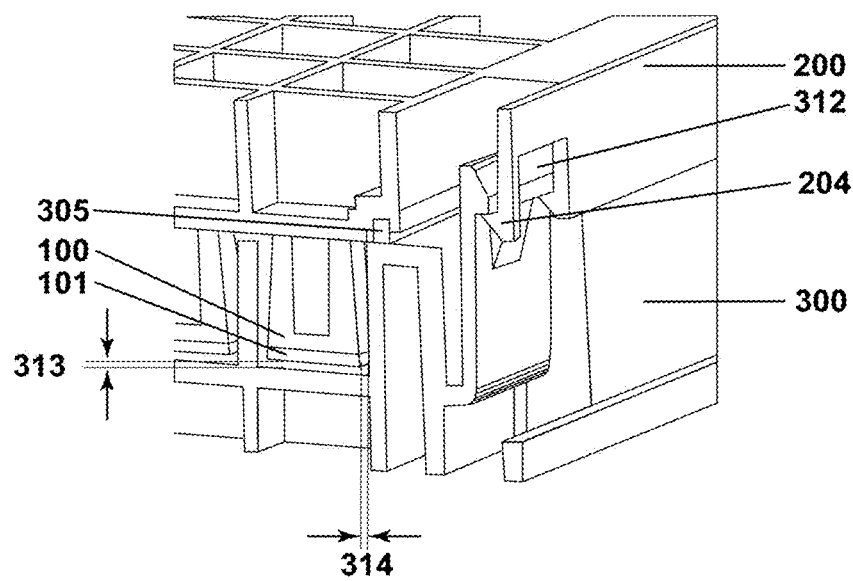
FIG. 11 illustrates a close up view of the details (i.e. clamping features, sample gap, well gap, etc.) in a hybridization assembly.

In another embodiment, an HT assembly, as depicted in FIG. 11, includes a sensor plate (200). The sensor plate includes a flexable member, i.e. gasket (305) that surrounds all the support members. The HT plate (300) is a hybridization plate as described in the previous section without a sealing surface. The placement, shape, dimensions, or design of the gasket can be, for example, dependent on the dimensions of the holding device, operating temperature and vapor pressure of the liquid sample contained in the wells and so forth. The placement of the gasket from the edge of the holding device surface can be about 1 mm to about 10 mm. The gasket may also be formed on the holding device by any standard technique such as, for example, over molding, bonding with a pre-formed part, machining and the like. In one embodiment, the sensor plate includes a gasket that is made of any material known in the art such as a Thermal Plastic Elastomer (TPE) over-mold seal and the like.

Furthermore, the sensor plate can further include a plurality of clamping features (204). These features on the sensor plate connect to corresponding clamping features (312) on the hybridization plate to assure that the pieces are connected. There are alignment pins on the hybridization plate and corresponding alignment holes on the sensor plate to make sure that the parts are assembled in the proper orientation. The HT plate, for example, can be a hybridization plate, an assay plate, a detection plate or a shipping plate. The dimensions of the sample gap (313), as shown in FIG. 11, which is the distance from the surface of the array attached to the support member to the bottom of the well can be between 50 microns to 3,000 microns, or between 200 microns to 2,000 microns, or about 700 microns in distance. The dimensions of the well gap (314) which is the distance from the side of the support member to the side wall of the well can be between 50 microns to 3,000 microns in distance, or between 200 microns to 2,000 microns, or about 900 microns in distance. In some embodiments, a HT assembly is designed such that a hybridization solution volume of less than 100 µl can be used, or about 80 µl, or 50 µl can be used.

Stain Plate

Figure 12:
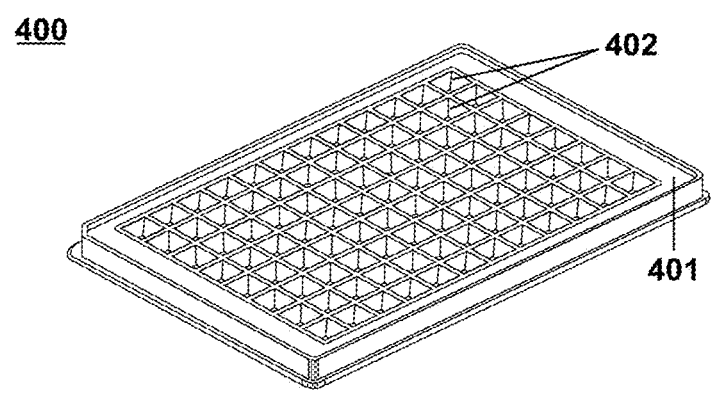
FIG. 12 illustrates a stain plate.

An exemplary stain plate (400), which is used for staining the arrays on the microarray plate (200), is illustrated in FIG. 12. The stain plate is a plate (401) with wells (402) designed to receive the arrays on the microarray plate. The stain plate includes at least two wells that are optimally designed to hold a minimum volume of stain to be in contact with the array surface of the arrays on the array plate.

Wash Plate

Figure 13A:
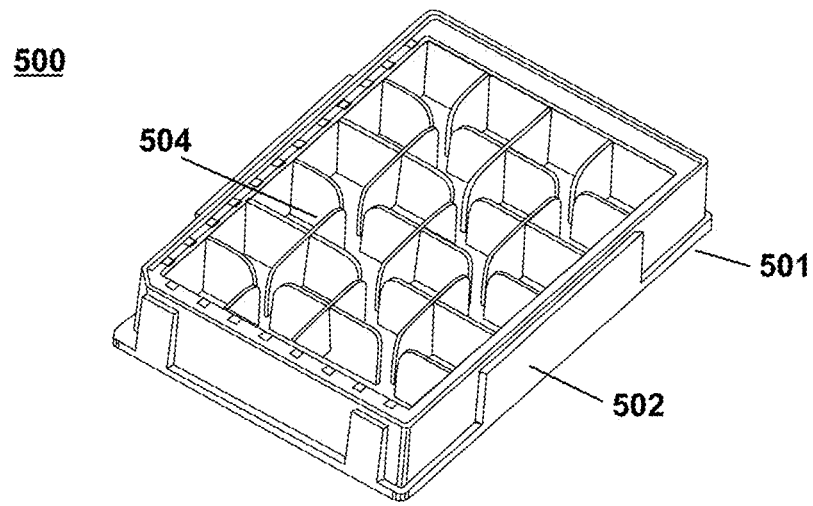
FIG. 13A shows a top view and FIG. 13B shows a bottom view of the wash plate.
Figure 13B:
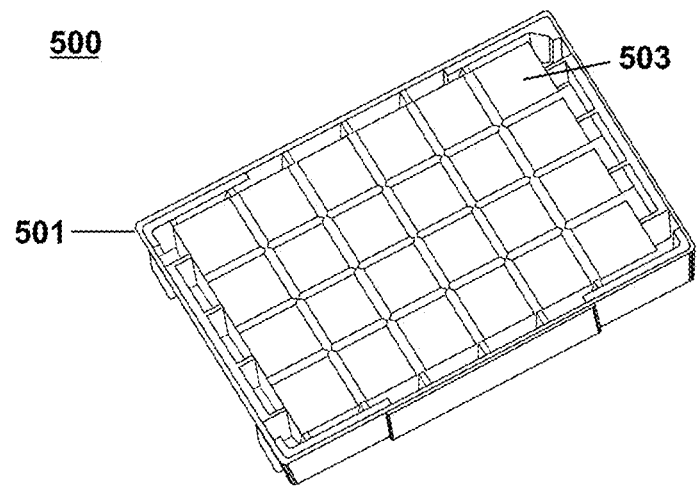

An exemplary wash plate (500) which is used for washing the microarray plate (200) is illustrated in FIGS. 13A and 13B. The wash plate is a plate (501) with wells (502) designed to receive the arrays on the microarray plate. The washing plate includes at least two wells optimally designed to hold a sufficient amount of volume to efficiently wash the array(s).

In one embodiment, a wash plate with an open well design, where the fluid is dispensed equally across all the wells, is provided. An example of a wash plate is shown in FIG. 13A. The partition (504) is optimized to improve the washing efficiency between the pegs. The partition can include vents or slits on the walls to promote even fluid flow across all the wells. Opening up the wells can be desired such that the wash solution is contained throughout the wells. In one embodiment, there are 24 wells to contain 96 sensor pegs (4 sensor pegs per well). In another embodiment, there are no wells.

Detection Plate

Figure 14A:
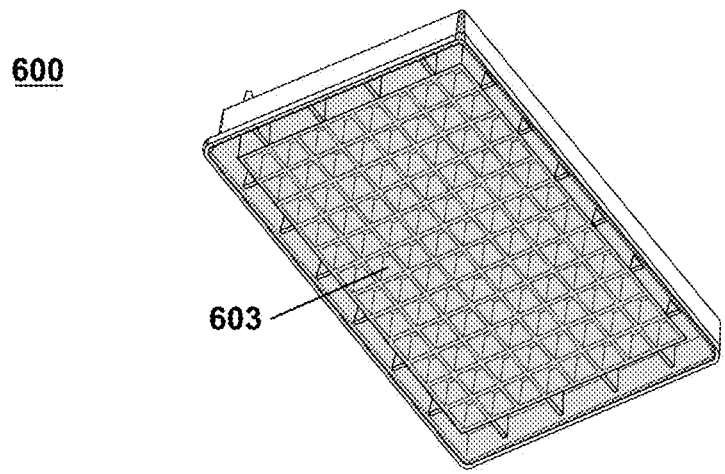
FIG. 14A shows a bottom view and FIG. 14B shows a top view of the detection plate.
Figure 14B:
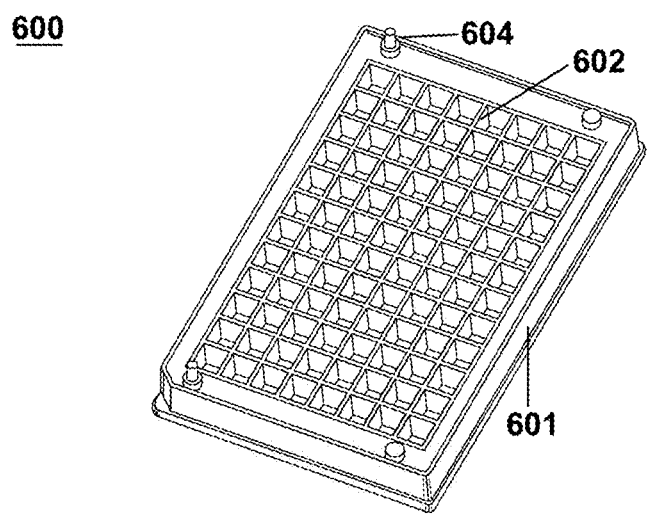

The detection plate (600), which is used for processing the microarray plate (200) during the scanning process, is illustrated in FIG. 14A. The detection plate is a plate (601) with wells (602) designed to receive the arrays on the microarray plate. The detection plate, as shown in FIG. 14B, includes a window made of an optically clear and low-fluorescence material (603), such as fused silica, zeonor (zionex), etc. After the hybridization process, the microarray plate is transferred and assembled with the scanning plate. In one embodiment, the detection plate includes positioning features (604) along the border of the plate to assist in matching the microarray plate to the detection plate. The positioning features (604) assure that the microarray plate is positioned precisely onto the detection plate for high resolution scanning. The positioning features enables alignment in the x, y and z directions. As shown in FIG. 14B, the positioning features include a surface to control the z coordinate. In one aspect, a plate includes at least two positioning features. The dimension of the gap from the surface of the sensor to the optically clear window can be between 100 microns to 2,000 microns, or about 600 microns. The optically clear window at the bottom of the detection plate must be transparent and distortion free for purposes of imaging the surface of the microarrays. It may be desirable that this material is non-fluorescent in order to minimize the background signal level and allow detection of low level signals from low intensity features of the probe array. A multi-plastic molded design can be applied to produce the hybridization and detection plates at very low cost.

In one embodiment, the material of the plate (601) of the detection plate (600) can be black or a dark color to minimize reflection during scanning and the optically clear window is made out of fused silica. The immersed sensors in buffer can be imaged and scanned with a microarray plate scanning instrument.

Reagent Plate

A reagent plate is used for storing and processing the reagents with the microarray plate (200) during the assay. The reagent plate can include a plate with wells designed to receive the arrays on the microarray plate. The reagent plate may include a sealable material that containes the reagent in the wells before use.

Shipping Plate

Figure 15A:
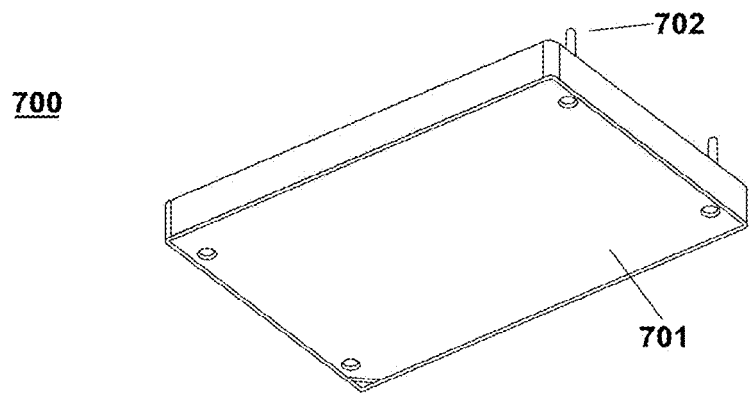
FIG. 15A shows a bottom view and FIG. 15B shows a top view of the package plate.
Figure 15B:
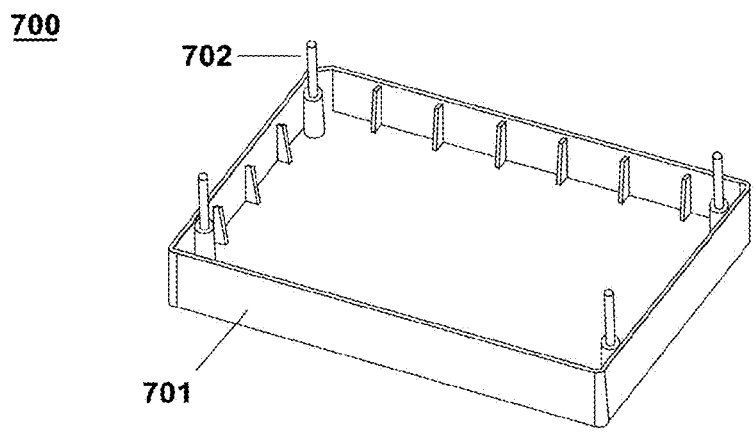
Figure 16:
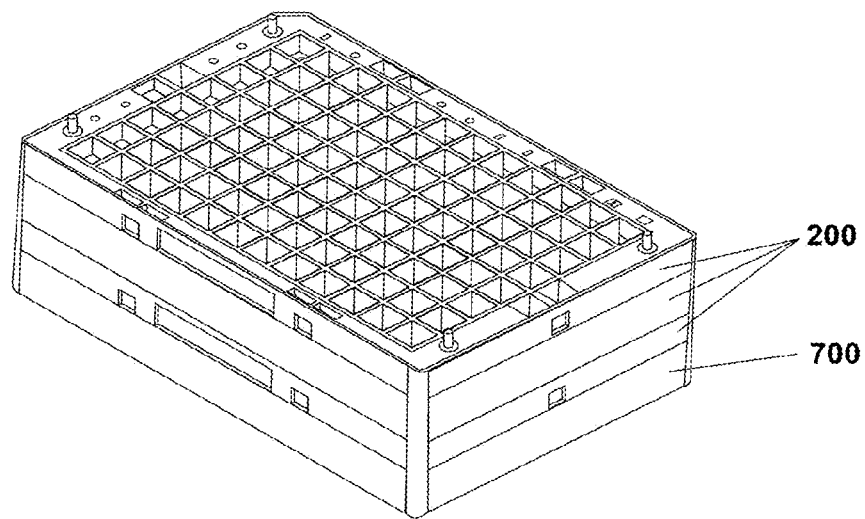
FIG. 16 illustrates a stack of sensor plates assembled with a package plate.

Shipping plate (700), as illustrated in FIGS. 15A and 15B, is used for protecting the mircoarray plate (200) during the shipping process. The shipping plate is a plate (701) with features (702) designed to receive the arrays on the microarray plate. Microarray plates (200) protected by a shipping plate (700) are illustrated in FIG. 16.

Assay Protocol

The arrays and the liquid samples in the wells are maintained in contact for a period of time, sufficient for the desired chemical reaction to occur. The conditions for a reaction, such as, for example, period of time of contact, temperature, pH, salt concentration and so forth, are dependent on the nature of the chemical reaction, the nature of the chemical reactants including the liquid samples, and the like. The conditions for binding of members of specific binding pairs are generally well known and will not be discussed in detail here.

The concept of using separate HT plates for hybridization (and high temperature washing) and scanning enables higher efficiency washes and cleaner images when executing the protocol. In one embodiment, all three components in the kit (a hybridization plate, a washing plate, staining plate and a detection plate) are disposable so durability and cleanliness is not a requirement beyond its single use. However, since the critical process steps are performed in separate wells, contamination during sequential steps is minimized or eliminated. In addition the transfer of the sensor plates between steps should facilitate more efficient cleaning of the arrays.

The hybridization and high temperature washes are performed in the wells of these HT plates which are designed to be assembled with the sensor plates. In order to minimize the fluidic volume of sample used during hybridization, the sensor plate is designed to minimize the spacing between the immersed array and the well bottom.

Normal washing that does not require high temperature incubation, since wash plates will work at a maximum temperature of 70° C., can be done in standard deep well plates which are also very economical in price since they are commercially available. These commercially available well plates have very large size wells for standard DI water or buffer solutions. Following hybridization and any other steps requiring rinsing or washing, the sensor plates can be immersed into these deep well plates for cleaning. Since the wash fluid volume is large, the cleaning process is more efficient and fewer wash steps would be required, thus saving further process time.

In one aspect, the sensor plate (200) is placed into the HT plate (for example, the hybridization plate, washing plate, staining plate, detection plate, reagent plate or packaging plate) filled with the desired liquid to contact the sensor, for example a microarray, with the liquid. When a sensor plate (200) has completed the hybridization, labeling and washing steps, the sensor plate can finally be immersed into the detection plate with clean buffer for scanning.

The additional advantage of this sensor plate concept is the ability to implement the same protocol manually by a laboratory technician instead of an automated High Throughput System (HTS) liquid handling instrument. With this interchangeable well plate concept, it could be possible for a single laboratory technician to process, for example, 96 arrays through the hybridization protocol in approximately the same time as it would be to process a few cartridges with the current available tools.

Any person skilled in the art could understand that there is not a minimum length for the support members of the sensor plate. However, there may be a practical minimum length. A longer support member may allow simpler washing and staining as the array can be immersed deeper.

It is also understood by any person skilled in the art that that there are not limitations as to the size of the sensors attached to the support members. For example a 1 mm by 1 mm embodiment of sensor (101) can be mounted on the support members. However, the sensors can be smaller or longer than this.

In one aspect, a hybridization volume, for example for a 6.3 mm by 6.3 mm embodiment of a sensor (101), can be designed to be about 12 µl. However, there are no design constraints that would prevent a smaller volume. It is also understood by any person skilled in the art, that the detection plate described is not volume sensitive. Buffer is used as a coupling fluid between the sensors and the bottom of the detection plate, and its total volume is incidental. However, the distance from sensors to the outside surface of the detection plate may need to be kept very small if the scanner objective lens has a short focal length.

It is further understood by any person skilled in the art, that the transparent window of the detection plate of the application has a low fluorescence back-ground. In one example, a scanner with no detection plates has a background of 7 counts, which is a unit of measure of the background noise. The detection plate has a total fluorescence background of 14 counts. The dynamic range of the scanner is about 65,000 counts. A maximum acceptable fluorescence background for the window of the detection plate has not been established.

U.S. patent application Ser. Nos. 11/243,621 (U.S. Patent Application Publication No. 2006-008863, abandoned), filed on Sep. 4, 2005, 10/325,171 (abandoned), filed on Dec. 19, 2002, 10/428,626 (abandoned), filed on May 2, 1003, 10/456, 370, filed on Jun. 6, 2003, and 10/738,535 (abandoned), filed on Dec. 16, 2003, describe each different aspect of constructing sensor plates. Each of these applications is hereby incorporated by reference herein in their entirety for all purposes.

Hybridization Device, Method, and System using Mixing Beads

According to one aspect, a method, device and system are provided for hybridizing a target oligonucleotide to a complementary probe on at least one array. A first substrate including a support member with at least one array attached to a first end of the support member is provided. A second substrate including a container, such as a well, is also provided. A plurality of mixing beads is placed into the well of the second container. A solution with the target oligonucleotide is added to the well with the plurality of mixing beads. The first substrate is oriented above the second substrate such that an array attached to the first end of the support member on the first substrate can be dipped into the solution in the well of the second container. The mixing beads may be agitated before or during or after the array is dipped into the solution. Thereby, the solution is mixing while the target oligonucleotide is hybridizing to a complementary probe on the array.

This hybridizaton method may increase hybridization efficiency as expressed in more target being hybridized to complementary probes on an array and or reduced hybridization time required to achieve optimal hybridization kinetics. This hybridization mixing may enable for greater assay sensitivity by allowing more complementary target hybridize and hence a high stoichiometry of reporting molecules being non-covalently bound to an array feature. This greater sensitivity also allows for potentially reduced amount and or concentration of the target in the hybridization container and hence enables for lower amplification yield requirements in the target generation process.

In another aspect, this hybridization mixing method may reduce bubbles or may eliminate the negative effect of bubbles on the array. The agitation of the beads allows sufficient movement of the solution such that the bubbles, contained air, or foam diffuse at the surface of the liquid or has minimal affect on the surface of the array.

Figure 17A:
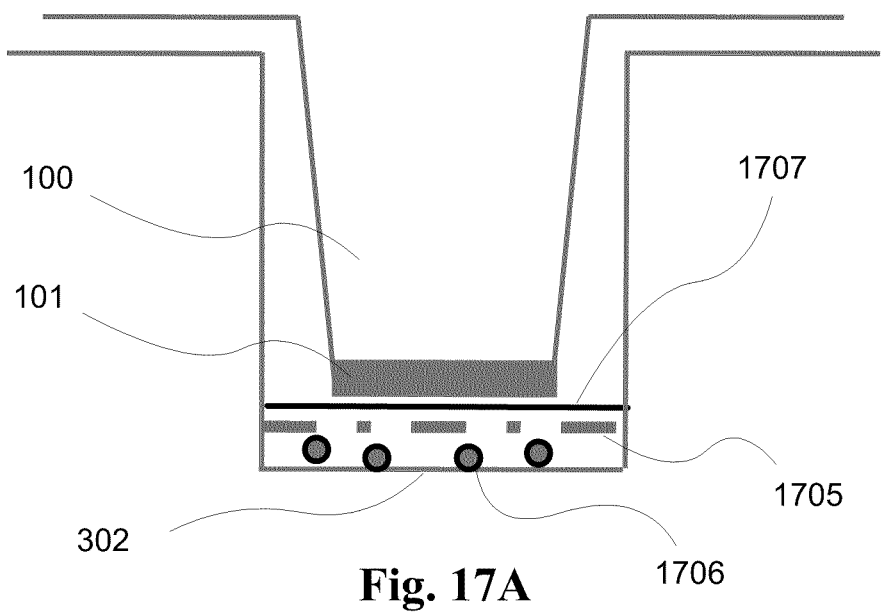
FIGS. 17A and 17B illustrate mixing devices comprising a plurality of mixing beads according to an embodiment.
Figure 17B:
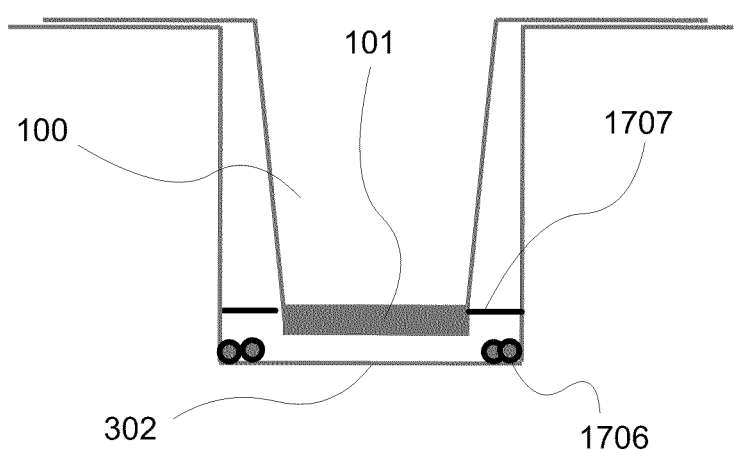

According to one aspect, a mixing device, as depicted in FIGS. 17A and 17B, includes a hybridization container (302) of a hybridization plate (300), mixing beads (1706) and optionally a permeable barrier (1705). An array (101) that is attached at the end of a support member (100) is provided. The hybridization container (302) comprises a plurality of mixing beads (1706) which are used to mix the target solution (1707). The mixing beads may be agitated before, during, or after the array attached to the end of the support member is dipped into the solution. The target oligonucleotide is hybridizing to the complementary probe on the array surface while the mixing beads are agitating.

Figure 18:
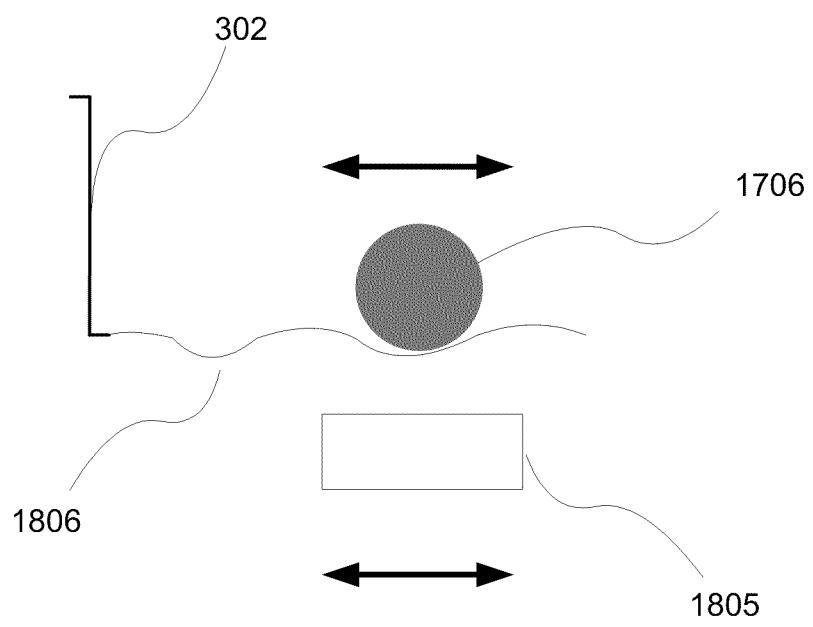
FIG. 18 illustrates an example of a method where a physical magnet is used to agitate a mixing bead according to an embodiment.

The hybridization container can be for example, a chamber, a well, a cuvette, a tube, and the like. The hybridization chamber can be part of a device, for example, a cartridge, hybridization plate, strip, and a lab card and the like. The planar openings of the containers, such as wells, may be of any shape, for example, a rectangular, square, circular, oval, elliptical, rectangular or square with rounded corners and so forth. The bottom of the wells may be level, conical, or slanted as discussed previously. In another embodiment, a surface in which the mixing beads are drawn across can comprise features (for example, channels, ridges, curved, pockets, bumps, etc.) to cause the mixing beads to move in the Z axis during agitation. The bottom surface of the wells can be curved, as illustrated in FIG. 18. In this embodiment, a magnet (1805) can be applied to move the mixing beads in and out of the bottom portions of the curved surface while moving the mixing bead back and forth across the bottom of the well. The mixing bead, while moving across the bottom surface, over a curve, will move up and down causing additional agitation in the z direction. FIG. 18 illustrates a magnet (1805) being applied to move a bead (1706) back and forth over the curved surface (1806) of the hybridization container (302). Alternatively, the features can also act as a path to guide the mixing beads along a desired path across the array surface according to an embodiment.

According to another embodiment, the container may be used for a different step of the assay, for example, a wash or a stain step. The mixing of the solution during the process step may improve the reaction time, among other variables.

The mixing beads can be made of any inert material known in the art. The material must be compatible with the assay (i.e. no leaching). Those skilled in the art will recognize that there are various materials, for example, plastic, metal, glass and ceramic, etc. that the mixing beads can be made of and that the mixing beads may be manufactured in various corresponding shapes, for example, square, octagon, rectangle, cylinder, etc. In an alternate embodiment, the beads can be coated with a material that would make the beads compatible with the assay. Beads may be magnetic, paramagnetic, ferromagnetic, diamagnetic, etc. In another embodiment, the mixing beads are made from stainless steel, spherical in shape and are magnetic.

The volume of target solution is dependent on various factors, such as, the dimension of the array surface and the dimensions of the well. The volume of the target solution may be about 20 microliters to about 100 microliters, or about 40 microliters to about 80 microliters, or about 60 microliters. The diameter of the mixing beads is dependent on several factors, such as, the dimensions of the sensor, the dimensions of the well, and the volume of target hybridization solution to be mixed. The mixing beads may also be various sizes from microparticles to nanoparticles. The diameter of the mixing bead can be about 20 to about 400 microns, or the mixing bead diameter can be about 50 micron to about 150 microns. Alternatively, the mixing bead diameter can be approximately 90 microns. The number of mixing beads present per well or container is determined by several factors, such as, size of beads, volume of hybridization solution, configuration of the container, agitation method, etc. and can be empirically optimized by one of skill in the art.

Agitation of the mixing beads can be achieved using either mechanical agitation through linear displacement of the hybridization container against an X axis or for instance, through rotational displacement of the hybridization container through a centered point of origin creating for a rocking motion or swirling. The device which may comprise a plurality of wells, for example, a hybridization plate, can be mechanically agitated by, for example, moving the tray back and forth or rotating the tray at a single axis or at a single point. Alternatively, the mixing beads, when magnetic, can be agitated by using a physical magnet or by application of a magnetic field according to one embodiment. A magnet can be used to move the mixing beads in different configuration across the wafer (for example, back and forth (X axis), circles, randomly, and XY in all directions). The magnet can be fixed, while the plate is mechanically moved. Alternately, the plate can be fixed, while the magnet is mechanically moved in the desired mixing configuration. The magnetic mixing beads can also be agitated by an electro-magnetic field alternating + and − polarity at appropriate frequency. The magnetic field can be, for example, at the opposite ends of a hybridization plate (i.e., top and bottom, one side and the other side). FIG. 17B illustrates a method where the mixing beads are moved along the bottom perimeter surface of the well. An electro-magnetic field alternating + and − polarity in a circle will cause the mixing beads to agitate the hybridization solution while staying at the bottom of the well. In this example, a permeable barrier may not be required if the electro-magnetic field keeps the beads contained at the bottom of the well. Those skilled in the art will recognize that there are other various mixing methods, such as sonication, etc.

According to another embodiment, a magnetic field is used to keep the mixing beads from contacting the array when the array is in contact with the target solution, for example, during hybridization. The final location of the beads can be in different locations of the container, depending on the characteristics of the container, the array, support member, etc. For example, the mixing beads can be attracted to the bottom surface, to the side, to a portion of the bottom and side, to multiple sides, to the end of a container, either during agitation, removal of the array, to change solutions, or other steps of the assay.

According to one aspect, the mixing beads may be physically enclosed in a sub-chamber by including an optional permeable barrier, i.e. mesh insert that precludes contact between the mixing beads and the array surface. The barrier prevents physical scratches or defects which may be physically damaged if the mixing beads contact the array surface while agitating or during other manipulations.

The permeable barrier is a material that can be permeated or penetrated, especially by liquids. The permeable barrier contains the beads in a sub chamber of the container, preventing the mixing beads from directly contacting the array surface. Those skilled in the art will recognize that there are various permeable barriers, for example, a mesh, membrane, nanofiber, etc. Those skilled in the art will recognize that there are various materials (for example, plastic, polyester, tape, cloth, paper, other polymers fiberglass, glass, metal such as stainless steel, aluminum, copper, and any combinations thereof, etc.) that the permeable barrier can be made of and that there are various corresponding methods of attaching (for example, adhesive, molding, soldering, etc.) the permeable barrier to the well. The permeable barrier can be made of any mesh material with pore sizes that are smaller than, i.e. various molecular weight cut-offs and the mixing bead diameter. The permeable barrier may be made out of material that is compatible with the assay, i.e. will not adsorb or otherwise bind critical components of the assay. Those skilled in the art will recognize that there are various openings (for example, square, rectangle, round, diamond, hexagonal, etc.) that the mesh can comprise. The permeable barrier can be attached in different locations of the well, depending on the characteristics of the container, the array, support member, etc. For example, the permeable barrier can be attached to the bottom of a well, to the side of the well, to a portion of the bottom surface and side of the well, to multiple sides of a well, to the end of a well, to the outlet/inlet of a well, i.e. chamber, etc. such that the target solution can be mixed by the movement of the mixing beads and flow freely through the permeable barrier, while having the permeable barrier contain the mixing beads. In another embodiment, the permeable barrier can be used to help drain the hybridization target solution without releasing the mixing beads.

According to one embodiment, the optional permeable barrier, for example, a mesh, can be assembled into a device by first molding part of a device that comprises the bottom of the containers wherein the mixing beads are placed. The mixing beads are then placed into the containers of the molded piece. A layer of mesh material can be incorporated onto the molded piece such that the layer of mesh is containing the mixing beads in the container. Another part of the device can then be molded on top such that the mesh is sandwiched between the two molded pieces. According to another embodiment, disposable mesh inserts with spacers are provided. The configuration of the disposable mesh insert may depend on the configuration of the container. Spacers, which provide a desired distance from the mesh and the well bottom, can be attached to the mesh. According to another embodiment, the mesh insert can in the shape of a container (i.e. box, cage, etc.) with the beads pre-filled. The mesh insert and or container are designed such that mesh contains the mixing beads at the bottom of the container.

In another embodiment, an optional permeable barrier is provided. The permeable barrier contains the beads in a sub chamber of the container. The permeable barrier precludes contact between the mixing beads and the array surface. In one embodiment, the permeable barrier is a mesh.

According to a further aspect, the mixing beads are magnetic. The agitation step comprises using a magnetic field to move the mixing beads to agitate the target solution. In an alternate embodiment, the agitation step comprises using a physical magnet to move the mixing beads to agitate the target solution. In another embodiment, the support members are pegs and the substrate is a hybridization plate.

According to another embodiment, the method, device and system comprises a plurality of encoded microparticles attached to the first end of the support member. The enclosed microparticles magnetic and are attached to the first end of the support member by applying a magnetic field.

It is to be understood that the description in this application is not restrictive. Many variations of the invention will be apparent to those of skill in the art upon reviewing the above description. Various alternatives, modifications and equivalents are possible. The description and figures are by way of illustration and not limitation. One of skill in the art would appreciate that the invention is not limited to the specific examples provided. In one embodiment of the invention, the system for processing sensor pegs includes various packages such as a sensor cartridge, a sensor plate and a sensor strip. The attached drawings illustrate some of the embodiments of these various sensor assemblies. All cited references, including patent and non-patent literature, are incorporated herewith by reference in their entireties for all purposes.

What is claimed is:
1. A method for hybridizing a target nucleic acid to a probe on an array, the method comprising:
providing a first substrate, wherein the first substrate comprises a support member, and wherein the array is attached to the support member;

providing a second substrate, wherein the second substrate comprises a container having a sub-chamber comprising a permeable barrier;

providing mixing beads, wherein the mixing beads are contained within the permeable barrier in the sub-chamber of the container such that a direct contact between the mixing beads and the surface of the array is prevented when the array is in the container;

adding a solution to the container, wherein the solution includes the target nucleic acid;

dipping the array into the solution; and hybridizing the target nucleic acid to the probe, wherein the hybridization includes agitation of the mixing beads, and wherein the agitation of the mixing beads additionally mixes the solution.

2. The method according to claim 1, wherein the mixing beads are about 20 to about 400 microns in diameter.

3. The method according to claim 2, wherein the permeable barrier is a mesh.

4. The method according to claim 1, wherein the mixing beads are magnetic.

5. The method according to claim 4, wherein the agitation of the mixing beads comprises applying a magnetic field to the mixing beads, and wherein said applying of the magnetic field to the mixing beads effectuates mixing of the solution.

6. The method according to claim 5, wherein said applying of the magnetic field further prevents the contact between the mixing beads and the array.

7. The method according to claim 4, wherein the mixing beads are made from stainless steel and are spherical in shape.

8. The method according to claim 1, wherein the support member is a peg.

9. The method according to claim 8, wherein the second substrate is a hybridization plate.

10. The method according to claim 1, wherein the first substrate further comprises a plurality of support members, wherein a plurality of arrays is attached to the plurality of support members, and wherein the second substrate further comprises a plurality of containers.

11. The method according to claim 1, wherein the mixing beads are about 50 to about 150 microns in diameter.

12. The method according to claim 1, wherein the mixing beads are about 90 microns in diameter.

13. The method according to claim 1, wherein the permeable barrier is a disposable mesh insert comprising spacers.

14. The method according to claim 1, wherein the permeable barrier is a mesh insert that encloses the mixing beads.

15. The method according to claim 1, wherein the container includes a surface comprising features that cause the mixing beads to move along a Z-axis of the container during the agitation step.

16. The method according to claim 15, wherein the surface comprising features is a curved surface or includes channels, ridges, pockets, or bumps.

17. The method according to claim 15, wherein the container is a well and a surface comprising features is located on the bottom of the well.

18. The method according to claim 1, wherein the volume of the solution added to the container is about 20 microliters to about 100 microliters.

19. The method according to claim 1, wherein the volume of the solution added to the container is about 40 microliters to about 80 microliters.

20. The method according to claim 1, wherein the volume of the solution added to the container is about 60 microliters.

* * * * *